US009585606B2

(12) United States Patent
Lisogurski

(10) Patent No.: US 9,585,606 B2
(45) Date of Patent: *Mar. 7, 2017

(54) OXIMETRY ASSEMBLY

(71) Applicant: Covidien LP, Boulder, CO (US)

(72) Inventor: Daniel Lisogurski, Boulder, CO (US)

(73) Assignee: Covidien LP, Boulder, CO (US)

(*) Notice: Subject to any disclaimer, the term of this patent is extended or adjusted under 35 U.S.C. 154(b) by 126 days.

This patent is subject to a terminal disclaimer.

(21) Appl. No.: 13/872,705

(22) Filed: Apr. 29, 2013

(65) Prior Publication Data

US 2013/0237783 A1 Sep. 12, 2013

Related U.S. Application Data

(63) Continuation of application No. 12/568,944, filed on Sep. 29, 2009.

(51) Int. Cl.
- *G01N 33/48* (2006.01)
- *A61B 5/1455* (2006.01)
- *G06F 19/00* (2011.01)

(52) U.S. Cl.
CPC ...... *A61B 5/14551* (2013.01); *A61B 5/14552* (2013.01); *G06F 19/3406* (2013.01); *G06F 19/3418* (2013.01); *A61B 2562/222* (2013.01); *A61B 2562/227* (2013.01)

(58) Field of Classification Search
None
See application file for complete search history.

(56) References Cited

U.S. PATENT DOCUMENTS

| | | |
|---|---|---|
| 3,638,640 A | 2/1972 | Shaw |
| 3,721,813 A | 3/1973 | Condon et al. |
| 4,332,006 A | 5/1982 | Choe |
| 4,360,860 A | 11/1982 | Johnston et al. |
| 4,703,161 A | 10/1987 | McLean |
| 4,714,341 A | 12/1987 | Hamaguri et al. |
| 4,805,623 A | 2/1989 | Jobsis |
| 4,807,631 A | 2/1989 | Hersh et al. |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |
| 5,035,243 A | 7/1991 | Muz |
| 5,065,749 A | 11/1991 | Hasebe et al. |
| 5,084,327 A | 1/1992 | Stengel |
| 5,094,240 A | 3/1992 | Muz |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,287,853 A | 2/1994 | Vester |
| 5,297,548 A | 3/1994 | Pologe |
| 5,348,003 A | 9/1994 | Caro |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,429,129 A | 7/1995 | Lovejoy et al. |
| 5,469,845 A | 11/1995 | DeLonzor et al. |
| 5,474,065 A | 12/1995 | Meathrel et al. |
| 5,482,036 A | 1/1996 | Diab et al. |
| 5,483,646 A | 1/1996 | Uchikoga |
| 5,511,546 A | 4/1996 | Hon |
| 5,553,614 A | 9/1996 | Chance |

(Continued)

FOREIGN PATENT DOCUMENTS

| | | |
|---|---|---|
| EP | 1309270 | 5/2003 |
| EP | 1574164 | 9/2005 |

(Continued)

OTHER PUBLICATIONS

Crilly, Paul. B., et al.; "An Integrated Pulse Oximeter System for Telemedicine Applications," IEEE Instrumentation and Measurement Technology Conference, Ottawa, Canada; May 19-21, 1997; pp. 102-104.

Rhee, Sokwoo, et al.,; "Design of an Artifact-Free Wearable Plethymographic Sensor," Proceedings of the First Joint BMES/EMBS Conference, Oct. 13-16, 1999, Atlanta, Georgia, p. 786.

Yao, Jianchu, et al; "Design of a Plug-and-Play Pulse Oximeter," Proceedings of the Second Joint EMBS/BMES Conference, Houston, Texas, Oct. 23-26, 2002; pp. 1752-1753.

Ostmark, Ake, et al.; "Mobile Medical Applications Made Feasible Through Use of EIS Platforms," IMTC-Instrumentation and Measurement Technology Conference, Vail, Colorado; May 20-22, 2003; pp. 292-295.

Wendelken, Suzanne, et al; "The Feasibility of Using a Forehead Reflectance Pulse Oximeter for Automated Remote Triage," IEEE, pp. 180-181 (2004).

Johnston, W.S., et al.; Extracting Breathing Rate Information from a Wearable Reflectance Pulse Oximeter Sensor, Proceedings of the 26$^{th}$ Annual International Conference of the IEEE EMBS, San Francicso, California; Sep. 1-5, 2004; pp. 5388-5391.

(Continued)

Primary Examiner — Pablo S Whaley

(57) ABSTRACT

Systems, methods, and devices for intercommunication between a medical sensor and an electronic patient monitor are provided. For example, one embodiment of a system for communicably coupling a medical sensor to an electronic patient monitor may include a sensor-side communication connector and a monitor-side communication connector. The sensor-side communication connector may be capable of receiving a raw physiological measurement signal from the medical sensor, and the monitor-side communication connector may be capable of providing a digital physiological measurement signal based at least in part on the raw physiological measurement signal to the electronic patient monitor via a data link.

13 Claims, 11 Drawing Sheets

(56) References Cited

U.S. PATENT DOCUMENTS

| | | |
|---|---|---|
| 5,564,417 A | 10/1996 | Chance |
| 5,575,285 A | 11/1996 | Takanashi et al. |
| 5,611,337 A | 3/1997 | Bukta |
| 5,619,992 A | 4/1997 | Guthrie et al. |
| 5,630,413 A | 5/1997 | Thomas et al. |
| 5,645,059 A | 7/1997 | Fein et al. |
| 5,645,060 A | 7/1997 | Yorkey |
| 5,666,952 A | 9/1997 | Fuse et al. |
| 5,680,857 A | 10/1997 | Pelikan et al. |
| 5,692,503 A | 12/1997 | Keunstner |
| 5,730,124 A | 3/1998 | Yamauchi |
| D393,830 S | 4/1998 | Tobler |
| 5,758,644 A | 6/1998 | Diab et al. |
| 5,779,631 A | 7/1998 | Chance |
| 5,786,592 A | 7/1998 | Hok |
| 5,807,247 A | 9/1998 | Merchant |
| 5,830,136 A | 11/1998 | DeLonzor et al. |
| 5,830,139 A | 11/1998 | Abreu |
| 5,831,598 A | 11/1998 | Kauffert et al. |
| 5,835,996 A | 11/1998 | Hashimoto |
| 5,842,981 A | 12/1998 | Larsen et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,139,488 A | 10/2000 | Ball |
| 6,144,444 A | 11/2000 | Haworth et al. |
| 6,150,951 A | 11/2000 | Olejniczak |
| 6,154,422 A | 11/2000 | Shinkawa et al. |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schollermann et al. |
| 6,230,035 B1 | 5/2001 | Aoyagi et al. |
| 6,243,654 B1 * | 6/2001 | Johnson et al. ............ 702/85 |
| 6,253,098 B1 | 6/2001 | Walker et al. |
| 6,261,236 B1 | 7/2001 | Grimblatov |
| 6,266,546 B1 | 7/2001 | Steuer et al. |
| 6,285,895 B1 | 9/2001 | Ristolainen et al. |
| 6,298,252 B1 | 10/2001 | Kovach |
| 6,308,089 B1 | 10/2001 | von der Ruhr |
| 6,312,393 B1 | 11/2001 | Abreu |
| 6,349,228 B1 | 2/2002 | Kiani et al. |
| 6,353,750 B1 | 3/2002 | Kimura et al. |
| 6,375,609 B1 | 4/2002 | Hastings |
| 6,397,091 B2 | 5/2002 | Diab et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,483,781 B2 | 11/2002 | Igarashi |
| 6,487,439 B1 | 11/2002 | Skladnev et al. |
| 6,490,466 B1 | 12/2002 | Fein |
| 6,501,974 B2 | 12/2002 | Huiku |
| 6,501,975 B2 | 12/2002 | Diab et al. |
| 6,512,937 B2 | 1/2003 | Blank et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,564,088 B1 | 5/2003 | Soller et al. |
| 6,571,113 B1 | 5/2003 | Fein |
| 6,580,086 B1 | 6/2003 | Schulz et al. |
| 6,584,336 B1 | 6/2003 | Ali |
| 6,589,172 B2 | 7/2003 | Williams et al. |
| 6,591,122 B2 | 7/2003 | Schmitt |
| 6,594,513 B1 | 7/2003 | Jobsis et al. |
| 6,605,510 B2 | 8/2003 | Watatani |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kiani |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,675,031 B1 | 1/2004 | Porges |
| 6,678,543 B2 | 1/2004 | Diab et al. |
| 6,684,090 B2 | 1/2004 | Ali et al. |
| 6,690,958 B1 | 2/2004 | Walker et al. |
| 6,697,655 B2 | 2/2004 | Sueppel et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,750,971 B2 | 6/2004 | Overbeck |
| 6,770,028 B1 | 8/2004 | Ali |
| 6,785,568 B2 | 8/2004 | Chance |
| 6,791,689 B1 | 9/2004 | Weckstrom |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,850,053 B2 | 2/2005 | Daalmans et al. |
| 6,850,788 B2 | 2/2005 | Al-Ali |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,916,289 B2 | 7/2005 | Schnall |
| 6,930,403 B2 | 8/2005 | Hartman et al. |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,971,580 B2 | 12/2005 | Zhu et al. |
| 6,983,178 B2 | 1/2006 | Fine et al. |
| 6,992,751 B2 | 1/2006 | Okita et al. |
| 6,993,371 B2 | 1/2006 | Kiani et al. |
| 6,996,427 B2 | 2/2006 | Ali et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,679 B2 | 4/2006 | Addison |
| 7,035,697 B1 | 4/2006 | Brown |
| 7,047,056 B2 | 5/2006 | Hannula et al. |
| 7,102,964 B2 | 9/2006 | Fujisawa |
| 7,127,278 B2 | 10/2006 | Melker et al. |
| 7,154,398 B2 | 12/2006 | Chen et al. |
| 7,154,816 B2 | 12/2006 | Igarashi et al. |
| 7,162,306 B2 | 1/2007 | Caby et al. |
| 7,198,778 B2 | 4/2007 | Achilefu et al. |
| 7,204,041 B1 | 4/2007 | Bailey et al. |
| 7,209,775 B2 | 4/2007 | Bae et al. |
| 7,229,188 B2 | 6/2007 | Mah |
| 7,232,238 B2 | 6/2007 | Long et al. |
| 7,236,811 B2 | 6/2007 | Schmitt |
| 7,263,395 B2 | 8/2007 | Chan et al. |
| 7,272,426 B2 | 9/2007 | Schmid |
| 7,371,981 B2 | 5/2008 | Abdul-Hafiz |
| 7,373,193 B2 | 5/2008 | Al-Ali et al. |
| 7,382,263 B2 | 6/2008 | Danowski et al. |
| 7,469,158 B2 | 12/2008 | Cutler et al. |
| 7,483,729 B2 | 1/2009 | Al-Ali et al. |
| 7,499,740 B2 | 3/2009 | Nordstrom |
| 7,509,494 B2 * | 3/2009 | Al-Ali .................. 713/168 |
| 7,572,229 B2 | 8/2009 | Yeo et al. |

(56) References Cited

U.S. PATENT DOCUMENTS

| | | |
|---|---|---|
| 7,574,244 B2 | 8/2009 | Eghbal et al. |
| 7,590,439 B2 | 9/2009 | Raridan |
| 8,060,170 B2 | 11/2011 | Mannheimer |
| 8,174,371 B2 | 5/2012 | Schwieger |
| 8,221,319 B2 | 7/2012 | Lovejoy |
| 8,255,029 B2 | 8/2012 | Addison |
| 8,315,683 B2 | 11/2012 | Al-Ali et al. |
| 8,353,842 B2 | 1/2013 | Al-Ali |
| 8,364,224 B2 | 1/2013 | Boyce et al. |
| 8,365,730 B2 | 2/2013 | Baker |
| 8,366,613 B2 | 2/2013 | Petersen |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0043512 A1 | 11/2001 | Igarashi |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0109808 A1 | 8/2002 | Sekiguchi |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0065269 A1 | 4/2003 | Vetter et al. |
| 2003/0120164 A1 | 6/2003 | Nielsen |
| 2003/0130590 A1 | 7/2003 | Bui et al. |
| 2003/0139687 A1 | 7/2003 | Abreu |
| 2003/0144584 A1 | 7/2003 | Mendelson |
| 2003/0184165 A1 | 10/2003 | Chiu |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0098009 A1 | 5/2004 | Boecker et al. |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0190383 A1 | 9/2004 | Marcucelli |
| 2004/0230106 A1 | 11/2004 | Schmitt et al. |
| 2004/0264304 A1 | 12/2004 | Furukawa |
| 2005/0065417 A1 | 3/2005 | Ali et al. |
| 2005/0075550 A1 | 4/2005 | Lindekugel |
| 2005/0080323 A1 | 4/2005 | Kato |
| 2005/0096561 A1 | 5/2005 | Conn |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0185513 A1 | 8/2005 | Tamura et al. |
| 2005/0192488 A1 | 9/2005 | Bryenton et al. |
| 2005/0197548 A1 | 9/2005 | Dietiker |
| 2005/0203357 A1 | 9/2005 | Debreczeny et al. |
| 2005/0228248 A1 | 10/2005 | Dietiker |
| 2005/0228298 A1 | 10/2005 | Banet et al. |
| 2005/0228301 A1 | 10/2005 | Banet et al. |
| 2005/0245839 A1 | 11/2005 | Stivoric et al. |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058594 A1 | 3/2006 | Ishizuka et al. |
| 2006/0058683 A1 | 3/2006 | Chance |
| 2006/0064024 A1 | 3/2006 | Schnall |
| 2006/0106323 A1 | 5/2006 | Bischoff et al. |
| 2006/0195028 A1 | 8/2006 | Hannula et al. |
| 2006/0224058 A1 | 10/2006 | Mannheimer et al. |
| 2006/0247501 A1 | 11/2006 | Ali |
| 2006/0250043 A1 | 11/2006 | Chung |
| 2006/0258921 A1 | 11/2006 | Addison et al. |
| 2007/0038155 A1 | 2/2007 | Kelly et al. |
| 2007/0043281 A1 | 2/2007 | Fine |
| 2007/0060786 A1 | 3/2007 | Gura et al. |
| 2007/0073121 A1 | 3/2007 | Hoarau et al. |
| 2007/0088207 A1 | 4/2007 | Mannheimer |
| 2007/0100222 A1 | 5/2007 | Mastrototaro et al. |
| 2007/0102928 A1 | 5/2007 | Yang |
| 2007/0167693 A1 | 7/2007 | Scholler et al. |
| 2007/0167850 A1 | 7/2007 | Russell et al. |
| 2007/0213621 A1 | 9/2007 | Reisfeld et al. |
| 2007/0213624 A1 | 9/2007 | Reisfeld et al. |
| 2007/0219430 A1 | 9/2007 | Moore |
| 2007/0232887 A1 | 10/2007 | Bettesh et al. |
| 2007/0276270 A1 | 11/2007 | Tran |
| 2008/0001735 A1 | 1/2008 | Tran |
| 2008/0004904 A1 | 1/2008 | Tran |
| 2008/0053456 A1 | 3/2008 | Brown et al. |
| 2008/0083065 A1 | 4/2008 | Bautovich |
| 2008/0097552 A1 | 4/2008 | Dicks |
| 2008/0097908 A1* | 4/2008 | Dicks .............. A61B 5/0022 705/50 |
| 2008/0167691 A1 | 7/2008 | Weintraub |
| 2009/0099423 A1 | 4/2009 | Al-Ali et al. |
| 2009/0171404 A1 | 7/2009 | Irani et al. |
| 2009/0247849 A1 | 10/2009 | McCutcheon |
| 2009/0247850 A1 | 10/2009 | Porges |
| 2009/0299157 A1 | 12/2009 | Telfort |
| 2009/0307392 A1 | 12/2009 | Mychalowych |
| 2009/0318779 A1 | 12/2009 | Tran |
| 2010/0081890 A1 | 4/2010 | Li |
| 2010/0277119 A1 | 11/2010 | Montague et al. |
| 2010/0317978 A1 | 12/2010 | Malle et al. |
| 2011/0066061 A1 | 3/2011 | Colman |
| 2011/0071370 A1 | 3/2011 | Al-Ali |
| 2011/0077473 A1 | 3/2011 | Lisogurski |
| 2011/0125063 A1 | 5/2011 | Shalon et al. |
| 2011/0152645 A1 | 6/2011 | Kiani |
| 2011/0187207 A1 | 8/2011 | Arnold et al. |
| 2011/0208010 A1 | 8/2011 | McKenna |
| 2012/0130239 A1 | 5/2012 | Meyer |
| 2012/0179015 A1 | 7/2012 | Mann et al. |

FOREIGN PATENT DOCUMENTS

| | | |
|---|---|---|
| EP | 2064989 | 3/2012 |
| GB | 2409951 | 7/2005 |
| JP | 6098881 | 4/1994 |
| JP | 6154177 | 6/1994 |
| JP | 2005034472 | 2/2005 |
| WO | WO9221281 | 12/1992 |
| WO | WO/93/09711 | * 5/1993 |
| WO | WO9309711 | 5/1993 |
| WO | WO9413198 | 6/1994 |
| WO | WO0021438 | 4/2000 |
| WO | WO2007109272 | 9/2007 |

OTHER PUBLICATIONS

Such, Hans Olaf; "Optoelectronic Non-Invasive Vascular Diagnostics Using Multiple Wavelength and Imaging Approach," Dissertation (1998).

Cysewska-Sobusaik, Anna; "Metrological Problems with Noninvasive Transillumination of Living Tissues," Proceedings of SPIE, vol. 4515, pp. 15-24 (2001).

Maletras, Francois-Xavier, et al.; "Construction and Calibration of a New Design of Fiber Optic Respiratory Plethysmograph (FORP),"

(56) References Cited

OTHER PUBLICATIONS

Optomechanical Design and Engineering, Proceedings of SPIE, vol. 4444, pp. 285-293 (2001).

Relente, A.R., et al.; "Characterization and Adaptive Filtering of Motion Artifacts in Pulse Oximetry using Accelerometers," Proceedings of the Second Joint EMBS/BMES Conference, Houston, Texas, Oct. 23-26, 2002; pp. 1769-1770.

Oadagiri, Y.; "Pulse Wave Measuring Device," Micromechatronics, vol. 42, No. 3, pp. 6-11 (undated) (Article in Japanese—contains English summary of Article).

Cyrill, D., et al.; "Adaptive Comb Filter for Quasi-Periodic Physiologic Signals," Proceedings of the $25^{th}$ Annual International Conference of the IEEE EMBS, Cancun, Mexico, Sep. 17-21, 2003; pp. 2439-2442.

* cited by examiner

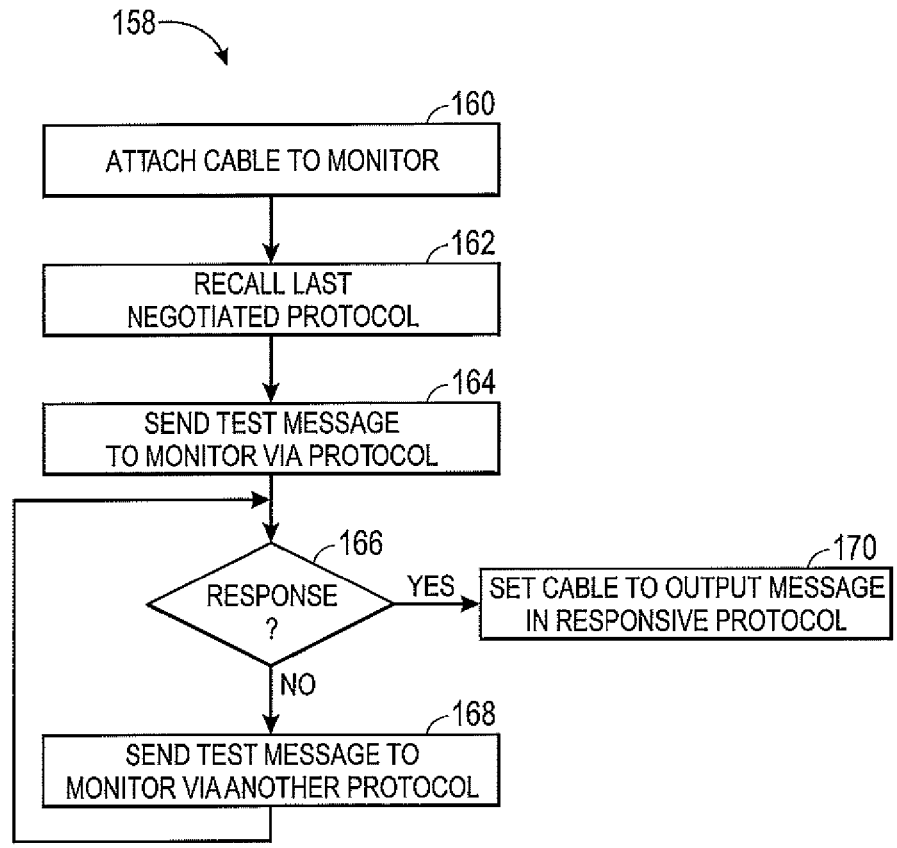
FIG. 14
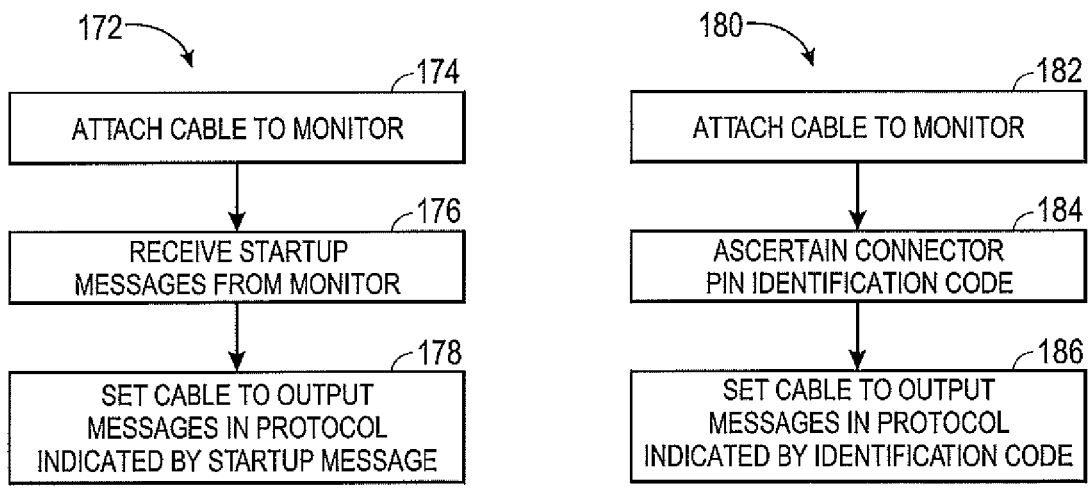
FIG. 15
FIG. 16

OXIMETRY ASSEMBLY

CROSS REFERENCE TO RELATED APPLICATIONS

The present application is a continuation of U.S. application Ser. No. 12/568,944, filed Sep. 29, 2009, which is hereby incorporated by reference in its entirety.

BACKGROUND

The presently disclosed subject matter relates generally to communicating data from a medical sensor to an electronic patient monitor and, more particularly, to communicating physiological measurements from data or instructions for obtaining physiological measurements from data to an electronic patient monitor.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Electronic patient monitors may be commonly used to monitor patient parameters such as ECG, pulse oximetry, blood pressure, and/or body temperature, among other things. Multi-parameter electronic patient monitors may be expensive electronic patient monitor units that display such patient parameters from a number of supported sensor types. To accommodate sensors from a variety of manufacturers, such monitors may be designed to employ a proprietary connector for each sensor type. The sensors may be attached to the monitor via the connector through a patient cable. The patient monitor may contain a dedicated circuit that acquires data from the sensor and may include a special module that specializes in the type of sensor. For example, a multi-parameter monitor may contain an Original Equipment Manufacturer (OEM) module to determine physiological measurements from a raw measurement. By way of example, within a single electronic patient monitor, a first OEM module from a first manufacturer may receive a raw signal from a photoplethysmographic sensor, determining pulse rate and/or oxygen saturation based on the raw signal. A second OEM module from a different manufacturer may receive a raw signal from a blood pressure cuff, determining blood pressure based on the raw signal.

The OEM modules in a multi-parameter monitor may be very difficult to upgrade, as the monitor may be disassembled before the OEM module is replaced. Thus, it may be unlikely for major upgrades to a patient monitor to occur once the patient monitor has been delivered to a medical facility. Accordingly, new developments, such as improved algorithms for obtaining physiological measurements from sensor data, may not easily be included in existing patient monitors. While some upgrades involve only firmware changes, the difficulty in upgrading is especially relevant when hardware or connector changes are required. In practice, expensive monitors are seldom upgraded in the field. Typically, another device is placed next to the old monitor, resulting in cluttered hospital environments and multiple displays for the caregivers to read. It may also be difficult to base alarm decisions on multiple monitors since they typically do not communicate with each other

SUMMARY

Certain aspects commensurate in scope with the originally claimed embodiments are set forth below. It should be understood that these aspects are presented merely to provide the reader with a brief summary of certain forms the embodiments might take and that these aspects are not intended to limit the scope of the presently disclosed subject matter. Indeed, the embodiments may encompass a variety of aspects that may not be set forth below.

Present embodiments relate to systems, methods, and devices for intercommunicating medical sensors and electronic patient monitors. For example, one embodiment of a system for communicably coupling a medical sensor to an electronic patient monitor may include a sensor-side communication connector and a monitor-side communication connector. The sensor-side communication connector may be capable of receiving a raw physiological measurement signal from the medical sensor, and the monitor-side communication connector may be capable of providing a digital physiological measurement signal based at least in part on the raw physiological measurement signal to the electronic patient monitor via a data link.

BRIEF DESCRIPTION OF THE DRAWINGS

Advantages of the presently disclosed subject matter may become apparent upon reading the following detailed description and upon reference to the drawings in which:

FIGS. 12-17 are flowcharts describing embodiments of methods for determining a protocol for communication between a patient cable and a patient monitor.

DETAILED DESCRIPTION

One or more specific embodiments of the present disclosure will be described below. In an effort to provide a concise description of these embodiments, not all features of an actual implementation are described in the specification.

It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments may apply to a variety of medical sensors, including photoplethysmographic sensors, temperature sensors, respiration bands, blood pressure sensors, electrocardiogram (ECG) sensors, electroencephalogram (EEG) sensors, pulse transit time sensors, and so forth. Such sensors may communicate with an electronic patient monitor using intercommunication circuitry such as a patient cable or a wireless connection. According to embodiments disclosed herein, sensor-monitor intercommunication circuitry may include instructions for obtaining physiological measurements from raw measurements. As such, an electronic patient monitor may receive a signal over a data link using a proprietary or universal protocol from such intercommunication circuitry, despite that a specific OEM board may not necessarily be installed within the receiving monitor. For example, the patient cable may transmit messages indicating the physiological measurements or provide instructions for obtaining the physiological measurements to the monitor using a protocol that may be proprietary to the monitor.

As used in the present disclosure, "instructions" that may be used for obtaining physiological measurements may refer to any information that enables the monitor to determine physiological characteristics of a patient from data collected by a medical sensor. Such instructions may include executable code (e.g., software) written specifically for the host processor of the monitor, or written to support any suitable processor type. The instructions could include a protocol whereby the processor is instructed to load such executable code and/or data memory to an absolute or relative address in the processor's memory. Additionally or alternatively, the instructions could include a high level script, which may be a proprietary format or an open format (e.g., Sun's JAVA language or Perl/Unix shell scripts), which is not processor-specific and which may instruct the processor to perform certain operations on the data.

Figure 1:
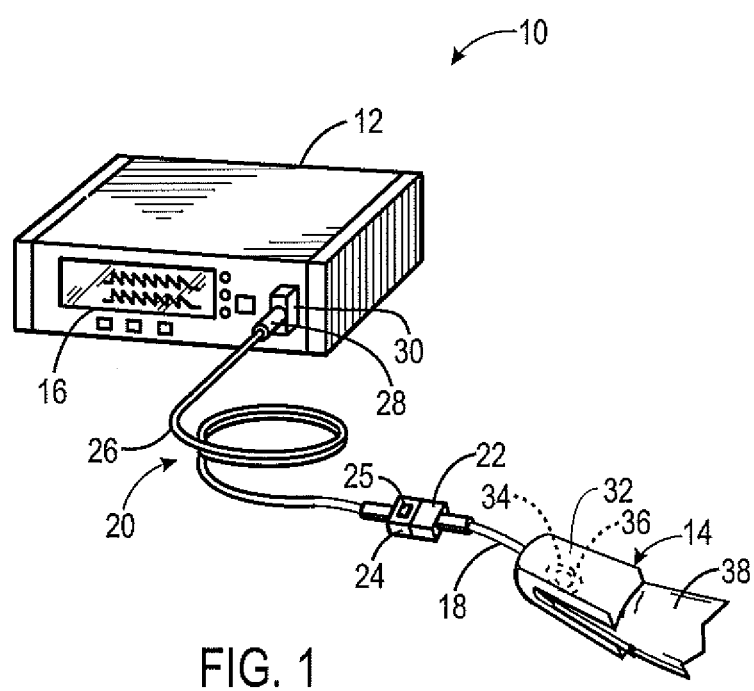
FIG. 1 is a schematic diagram of a system having instructions for sensor processing in sensor-monitor communication circuitry, in accordance with an embodiment.

With the foregoing in mind, FIG. 1 illustrates a perspective view of an embodiment of a sensor-monitor interconnection system 10 for communicably coupling an electronic patient monitor 12 to a medical sensor 14. Although the embodiment of the system 10 illustrated in FIG. 1 relates to photoplethysmography, the system 10 may be configured to obtain a variety of physiological measurements using a suitable medical sensor. For example, the system 10 may, additionally or alternatively, be configured to obtain a respiration rate, a patient temperature, an ECG, an EEG, a blood pressure, and/or a pulse transit time, and so forth.

The patient monitor 12 may communicate with the medical sensor 14 via a short analog cable 18 coupled to a sensor-monitor intercommunication cable 20. The patient monitor 12 may include a display 16, a memory, and various monitoring and control features. In certain embodiments, the patient monitor 12 may include a processor configured to receive software instructions from the sensor-monitor intercommunication cable 20. The software instructions may be employed by the processor in the patient monitor 12 to obtain physiological measurements, such as pulse rate or blood oxygen saturation, from raw photoplethysniographic data or other raw data that has been digitized within the sensor-monitor intercommunication cable 20. In other embodiments, the patient monitor 12 may not include a processor with such capabilities, but may rather be configured to display physiological measurements, such as pulse rate or blood oxygen saturation, that have been determined within the sensor-monitor intercommunication cable 20. For example, when the system 10 is configured for photoplethysmography, the sensor-monitor intercommunication cable 20 may include software instructions and/or capabilities for performing pulse oximetry measurements, calculations, and control algorithms, based on the sensor data received from the medical sensor 14.

In the presently illustrated embodiment of the system 10, the medical sensor 14 is a photoplethysmographic sensor. As should be appreciated, however, the sensor 14 may be a photoplethysmographic sensor, a temperature sensor, a respiration band, a blood pressure sensor, an arrhythmia sensor, a pulse transit time sensor, or any other suitable medical sensor. As noted above, the sensor 14 may include the short analog cable 18. The short analog cable 18 may include a sensor connector 22 that joins to a sensor-side cable connector 24 of the sensor-monitor intercommunication cable 20. The analog cable 18 may be of a sufficiently short length to prevent excessive interference before reaching the sensor-monitor intercommunication cable 20. The sensor-monitor intercommunication cable 20 may include the sensor-side cable connector 24, a monitor protocol selection button or switch 25, intercommunication cabling 26, and a monitor-side cable connector 28. The monitor-side cable connector 28 may join to a monitor connector 30 with a data communication link, such as a serial peripheral interface (SPI), a universal serial bus (USB) interface, a universal asynchronous receiver/transmitter (UART) interface, a Two Wire Interface (TWI) such as I2C, or an RS232 interface, or any other suitable communication link.

As described in greater detail below, the sensor-monitor intercommunication cable 20 may communicate with the monitor 12 using a protocol understandable by the monitor 12. Such protocols may include, for example, the Standard Host Interface Protocol (SHIP) or the Phillips Interface Protocol (PIP). The sensor-monitor intercommunication cable 20 may be preprogrammed to communicate using the protocol or may automatically select the particular protocol from among a variety of preprogrammed protocols, as described below with reference to FIGS. 12 and 13. Additionally or alternatively, a practitioner may manually set the protocol by pressing the button or switch 25 or selecting a setting on the button or switch 25. Thereafter, the sensor-monitor intercommunication cable 20 may communicate with the electronic patient monitor 12 and may not need to be specific to particular vendors or to particular sensors. Additionally or alternatively, the sensor-monitor intercommunication cable 20 may automatically negotiate a mutually supported protocol with the electronic patient monitor 12 or use other techniques to determine such a protocol, as generally described below with reference to FIGS. 12-17.

A sensor assembly or body 32 of the wireless medical sensor 14 may attach to patient tissue (e.g., a patient's finger, ear, forehead, or toe). In the illustrated embodiment, the sensor assembly 32 is configured to attach to a finger. The medical sensor 14, illustrated in the present embodiment as a photoplethysmographic sensor, may include an emitter 34 and a detector 36. When attached to pulsatile tissue of a patient 38, the emitter 34 may transmit light at certain wavelengths into the tissue and the detector 36 may receive the light after it has passed through or is reflected by the tissue. The amount of light that passes through the tissue and other characteristics of light waves may vary in accordance with the changing amount of certain blood constituents in the tissue and the related light absorption and/or scattering. For example, the emitter 34 may emit light from two or more LEDs or other suitable light sources into the pulsatile tissue. The reflected or transmitted light may be detected with the detector 36, such as a photodiode or photo-detector, after the light has passed through or has been reflected by the pulsatile tissue.

Figure 2:
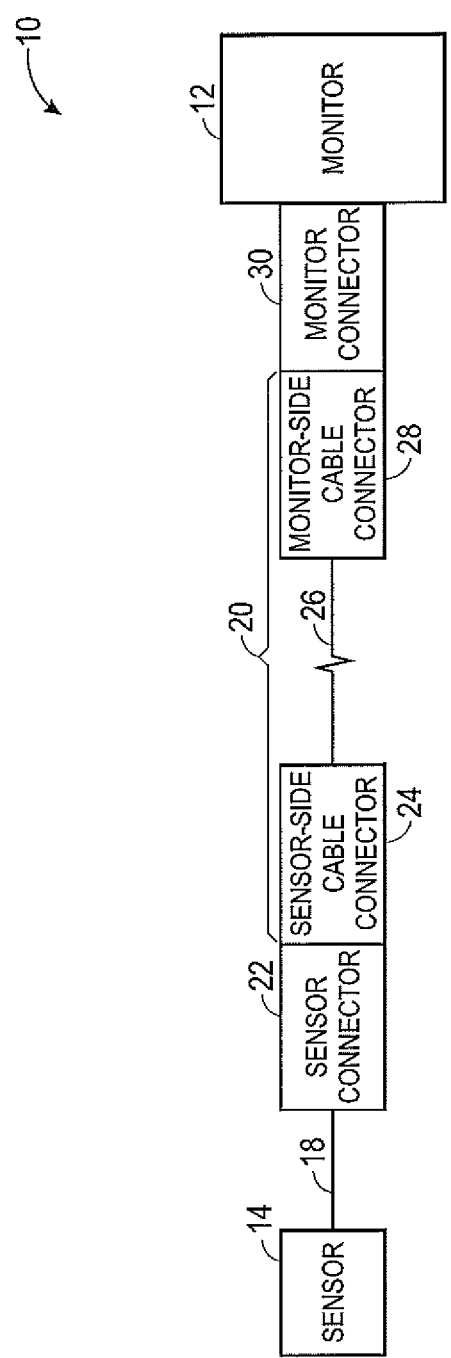
FIG. 2 is a block diagram of the system of FIG. 1, in accordance with an embodiment.

FIG. 2 is a simplified block diagram of the system 10 of FIG. 1. As illustrated in FIG. 2, the sensor 14 may connect to the patient monitor 12 by way of the sensor-monitor intercommunication cable 20. In particular, the sensor connector 22 of the analog cable 18 may connect to the sensor-side cable connector 24 of the sensor-monitor intercommunication cable 20. The sensor-side cable connector 24 may receive analog data from the medical sensor 14, digitize the data, and transmit the digitized data to the monitor-side cable connector 28 via the digital cable 26. One embodiment of the digital cable 26 may include minimal interconnecting cabling, which may include, for example, two power subcables and digital communication subcabling, as described below with reference to FIG. 4. It should be appreciated that the digital cable 26 may employ any suitable power cabling structures and/or techniques, and should not be understood to be limited to two power subcables.

In alternative embodiments, the sensor-side cable connector 24 may transmit the received analog data to the monitor-side cable connector 28 without first digitizing the data. With such alternative embodiments, the monitor-side cable connector 28 may instead digitize the analog data. If the sensor-side cable connector 24 does not first digitize the analog data before transmitting the data to the monitor-side cable connector 28, additional cabling and shielding may be employed to prevent attenuation and/or interference.

The monitor-side cable connector 28 may process the digitized data to obtain a physiological measurement, transmitting the determined physiological measurement to the patient monitor 12 via the monitor connector 30. Alternatively, the monitor-side cable connector 28 may transmit software instructions for obtaining the physiological measurements from the digitized data to the monitor 12. Thereafter, the monitor-side cable connector 28 may transmit the digitized data to the monitor 12 via the monitor connector 30, which may process the digitized data according to the received software instructions to obtain physiological measurements.

As described below, the monitor-side cable connector 28 may communicate with the monitor 12 via the monitor connector 30 using any suitable protocol. For example, the monitor 12 may only communicate via a single protocol, such as Phillips Interface Protocol (PIP), and the monitor-side cable connector 28 may communicate using the PIP protocol after automatically determining that messages sent to the monitor 12 be transmitted using the PIP protocol, as described below with reference to FIGS. 12-13, or after being manually set by a practitioner via the button or switch 25.

As described further below, the monitor-side cable connector 28 may autodetect the protocol by, for example, sending a command in a given protocol and waiting for a valid response. If no valid response is returned by the monitor 12 within a given time, and the monitor-side cable connector 28 may continue trying other protocols until a message type is found to which the monitor 12 responds.

After such an initial negotiation, the monitor-side cable connector 28 may stay in the negotiated protocol until power off. Additionally or alternatively, the monitor-side cable connector 28 may store the negotiated protocol in its non-volatile memory 62 and may remember the setting at next power up (reverting to negotiations only if the saved protocol fails). Additionally or alternatively, the monitor 12 may negotiate with the monitor-side cable connector 28. In some embodiments, the monitor 12 may identify its protocol at startup by sending a message type agreed on by several or all manufacturers of patient monitors. In some embodiments, certain connector pins may be connected to power or ground, or to specific resistors or voltages, through which the monitor-side cable connector 28 may identify the type of the monitor 12. Also, in some embodiments, the protocol may be determined during a USB device enumeration process.

The monitor connector 30 attached to the monitor 12 may represent a communication data link capable of communicating via one or more protocols. As noted above, the monitor connector 30 may include a serial peripheral interface (SPI), a universal serial bus (USB) interface, a universal asynchronous receiver/transmitter (DART) interface, a Two Wire Interface (TWI) such as I2C, or an RS232 interface, or any other suitable communication link. One embodiment of the pinout of the monitor connector 30 is described in greater detail below with reference FIG. 5.

Figure 3:
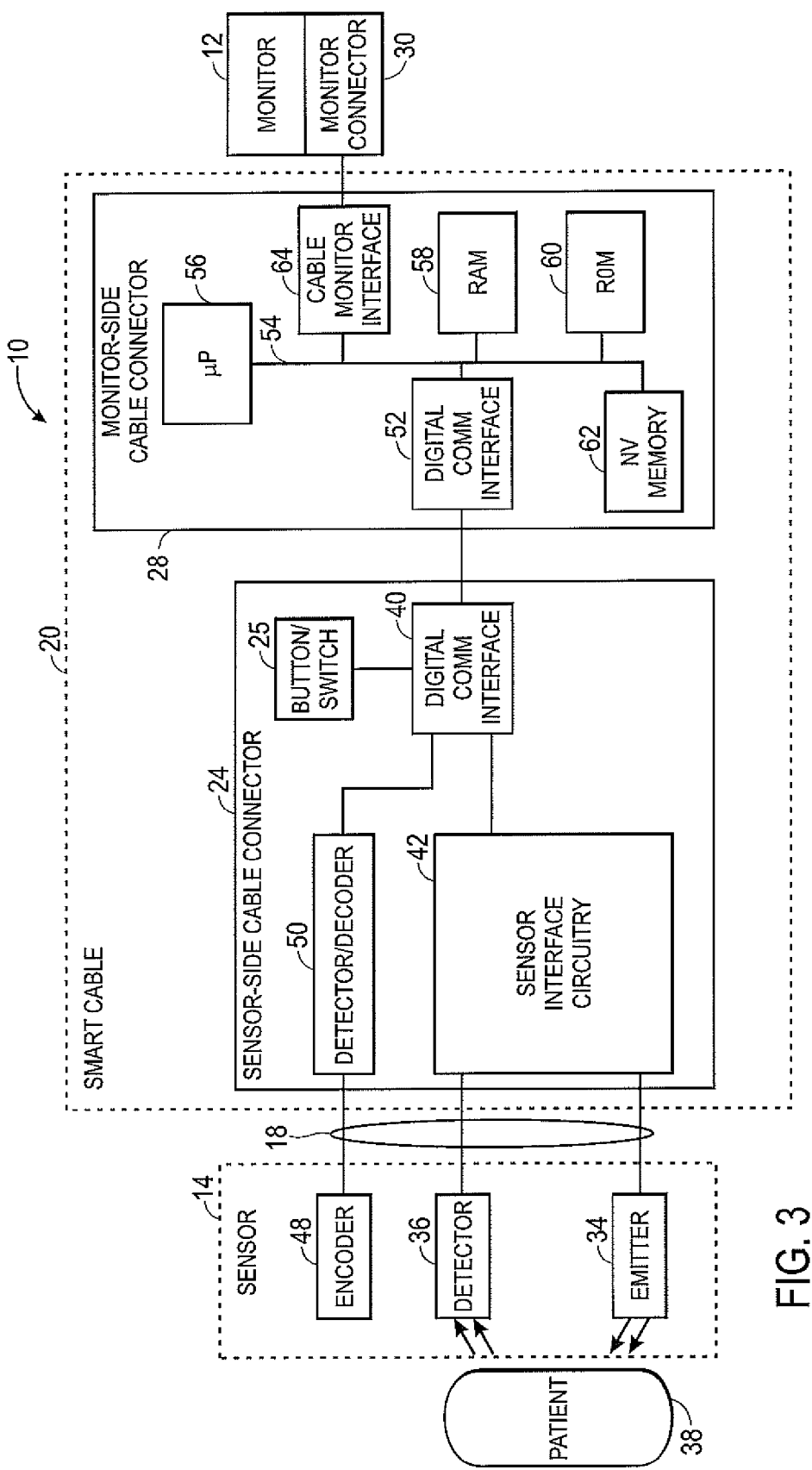
FIG. 3 is a more detailed block diagram of the system of FIG. 1, in accordance with an embodiment.

FIG. 3 is a more detailed block diagram of the system 10. By way of example, embodiments of the system 10 may be implemented with any suitable medical sensor and patient monitor, such as those available from Nellcor Puritan Bennett LLC. The system 10 may include the patient monitor 12, the sensor 14, and the sensor-monitor intercommunication cable 20, which may be configured to obtain, for example, a photoplethysmographic signal from patient tissue at certain predetermined wavelengths. The medical sensor 14 may be communicatively connected to the patient monitor 12 via the sensor-monitor intercommunication cable 20. When the system 10 is operating, light from the emitter 34, which may include one or more light emitting diodes (LEDs) of certain wavelengths, may pass into the patient 38 and be scattered and detected by the detector 36.

Specifically, the sensor 14 may be controlled by the signals from the sensor-side cable connector 24. A digital communication interface 40 may receive control signals from the monitor-side cable connection 28, which may control the manner in which sensor interface circuitry 42 controls the sensor 14. The sensor interface circuitry 42 may control the sensor 14 using any suitable pulse oximetry technique. In some embodiments, a time processing unit (TPU) may provide timing control signals to light drive circuitry. Such light drive circuitry may drive the emitter 34, controlling when the emitter 34 is illuminated, and if multiple light sources are used, the multiplexed timing for the different light sources. The sensor interface circuitry 42 may also receive signals from the detector 36. The signals from the detector 36 may represent raw analog data, which may be digitized by the sensor interface circuitry 42. In some embodiments, the sensor interface circuitry 42 may include, for example, an amplifier, a filter, and an analog to digital (A/D) converter circuit. The sensor interface circuitry 42 may sample these signals at the proper time, depending upon which of multiple light sources is illuminated, if multiple light sources are used. The sampled signals represent digitized raw data that may be, for example, a raw 16-bit digital stream of photoplethysmographic data sampled at 100 Hz.

In an embodiment, the sensor 14 may also contain an encoder 48 that provides signals indicative of the wavelength of one or more light sources of the emitter 34, which may allow for selection of appropriate calibration coefficients for calculating a physiological parameter such as blood oxygen saturation. The encoder 48 may, for instance, be a coded resistor, EEPROM or other coding devices (such as a capacitor, inductor, PROM, RFID, parallel resonant circuits, or a colorimetric indicator) that may provide a signal related to the characteristics of the medical sensor 14 that may indicate appropriate calibration characteristics for the photoplethysmographic sensor 14. Further, the encoder 48 may include encryption coding that prevents a disposable part of the photoplethysmographic sensor 14 from being recognized by a processor 38 that is not able to decode the encryption. For example, a detector/decoder 50 may be required to translate information from the encoder 48 before it can be properly processed to obtain physiological measurements from the digitized raw data output by the sensor interface circuitry 42.

Digital data from the detector/decoder 50 and/or the sensor interface circuitry 42 may be sent to the digital communication interface 40. Additionally, if present, the button or switch 25 may provide digital information to the digital communication interface 40 indicating the particular protocol with which the sensor-monitor intercommunication cable 20 should use to communicate with the electronic patient monitor 12. The digital communication interface 40 may coordinate the transmission of the digital data to the monitor-side cable connector 28. The digital data may be transmitted over the digital cable 26 and received by another digital communication interface 52 using any suitable protocol. For example, the digital communication interfaces 40 and 52 may communicate using, for example, a serial peripheral interface (SPI), a universal serial bus (USB) interface, a universal asynchronous receiver/transmitter (UART) interface, a Two Wire Interface (TWI) such as I2C, or an RS232 interface. The digital data may be provided to a bus 54 connected to a microprocessor 56.

In various embodiments, based at least in part upon the value of the received digitized raw data corresponding to the light received by detector 36, the microprocessor 56 may calculate a physiological parameter of interest using various algorithms. These algorithms may utilize coefficients, which may be empirically determined, corresponding to, for example, the wavelengths of light used. The algorithms may store interim values and other digital data in RAM 58. The algorithms and other software instructions for obtaining a physiological measurement based on the digitized data may be stored in ROM 60 or nonvolatile storage 62, which may include, for example, Flash memory. In a two-wavelength system, the particular set of coefficients chosen for any pair of wavelength spectra may be determined by the value indicated by the encoder 48 corresponding to a particular light source provided by the emitter 34. For example, the first wavelength may be a wavelength that is highly sensitive to small quantities of deoxyhemoglobin in blood, and the second wavelength may be a complimentary wavelength. Specifically, for example, such wavelengths may be produced by orange, red, infrared, green, and/or yellow LEDs. Different wavelengths may be selected based on instructions from the patient monitor 12, preferences stored in a nonvolatile storage 62. Such instructions or preferences may be selected at the patient monitor 12 by a switch on the patient monitor 12, a keyboard, or a port providing instructions from a remote host computer. Other software or instructions for carrying out the techniques described herein may also be stored on the nonvolatile memory 62, or may be stored on the ROM 60. The physiological measurements determined in the sensor-monitor intercommunication cable 20 may be encoded in a first protocol, which may or may not be proprietary to the sensor-monitor intercommunication cable 20. As described below, the physiological measurements may be translated from the first protocol into a second protocol understandable to the monitor 12, if the monitor 12 is not capable of understanding the first protocol.

After determining physiological measurements based on the received digitized raw data, the microprocessor 56 may communicate with the monitor 12 via a cable-monitor interface 64. The cable-monitor interface 64 may transmit these physiological measurements and/or the digitized raw data to the monitor 12 via the monitor connector 30. The sensor-monitor intercommunication cable 20 may communicate using messages in a protocol understandable by the electronic patient monitor 12. The protocol may be indicated by a selection made by the button or switch 25, or may be determined automatically by the sensor-monitor intercommunication cable 20, as described below with reference to FIGS. 12 and 13. In this way, the sensor-monitor intercommunication cable 20 may not need to be specific to a manufacturer or vendor.

It should be appreciated that the configuration of the sensor-monitor intercommunication cable 20 illustrated in FIG. 3 may vary. For example, certain circuitry of the sensor-side cable connector 24 may be incorporated into the monitor-side cable connector 28. If the sensor interface circuitry 42 is incorporated into the monitor-side cable connector 28, the cable 26 may transmit analog signals rather than digital signals, and additional shielding may be used to reduce attenuation and/or interference. Similarly, certain circuitry of the monitor-side cable connector 28 may be incorporated into the sensor-side cable connector 24, such as the microprocessor 56. If the microprocessor 56 is incorporated into the sensor-side cable connector 24, the sensor-side cable connector may have the capability to determine physiological measurements from the digitized data, which may be transmitted over the digital cable 26. In certain other embodiments, all or part of the circuitry of the sensor-monitor intercommunication cable 20 may be incorporated into the medical sensor 14. However, if the medical sensor 14 is a replaceable sensor, incorporating such circuitry into the sensor 14 may be costly. Moreover, as described below with reference to FIGS. 9 and 10, circuitry with the capabilities described above may be incorporated into other intercommunication links between the sensor 14 and the electronic patient monitor. For example, the circuitry may be incorporated into a separable cable connector or dangle, or into wireless adapters for joining the medical sensor 14 and the patient monitor 12.

Figure 4:
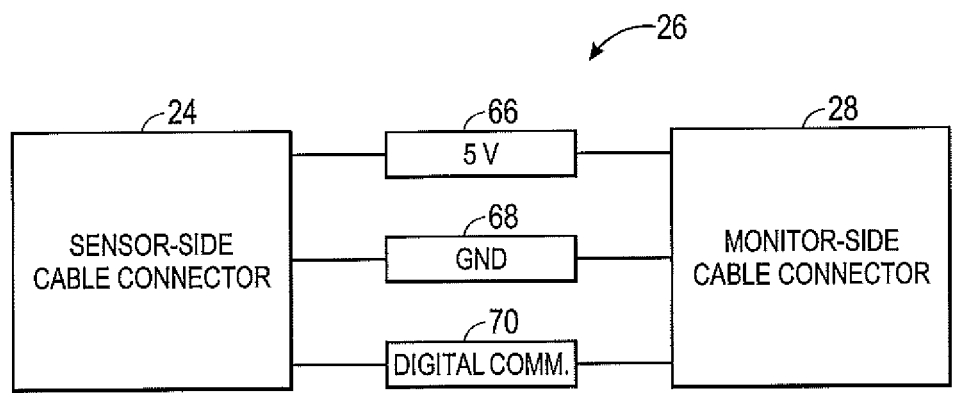
FIG. 4 is a block diagram of a cable connection to a medical sensor, in accordance with an embodiment.

FIG. 4 illustrates an exemplary configuration of an embodiment of the digital cable 26 between the sensor-side cable connector 24 and the monitor-side cable connector 28. Specifically, the digital cable 26 may include power, such as a 5V supply 66 in one particular embodiment, a ground line 68, and one or more digital communication lines 70. The digital communication lines may employ any suitable protocol for intercommunication of digital data between the sensor-side cable connector 24 and the monitor-side cable connector 28. For example, as noted above, such protocols may include serial peripheral interface (SPI), universal serial bus (USB), universal asynchronous receiver/transmitter (DART), a Two Wire Interface (TWI) such as I2C, or RS232 protocols.

The digital cable 26 may carry signals over the longest distance of the sensor-monitor intercommunication cable 20. By transmitting digital signals rather than analog, the digital cable 26 may not require as much shielding as a cable for transmitting an analog signal. Though some cable shielding may be employed to reduce electromagnetic emissions from the cable 26, the digitized signals may be much less likely to be corrupted by electromagnetic noise than low amplitude sensor outputs. Moreover, digital errors over the digital cable 26 may be detected, corrected, or may trigger data re-transmission in communications between the sensor-side cable connector 24 and the monitor-side cable connector 28.

Figure 5:
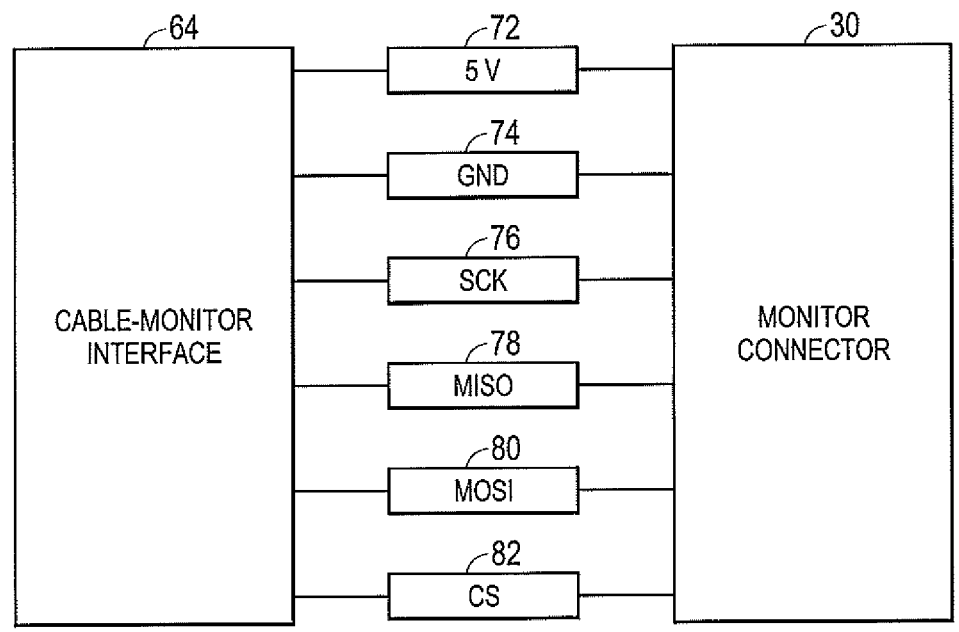
FIG. 5 is a block diagram of a data link to a patient monitor, in accordance with an embodiment.

FIG. 5 illustrates an exemplary configuration of an embodiment of the pinout interconnections between the cable-monitor interface 64 of the monitor-side cable connector 28 and the monitor connector 30. The pinout configuration may employ any suitable protocol for intercommunication of digital data between the cable-monitor interface 64 and the monitor connector 30. For example, as noted above, such protocols may include serial peripheral interface (SPI), universal serial bus (USB), universal asynchronous receiver/transmitter (DART), a Two Wire Interface (TWI) such as I2C, or RS232 protocols.

In the instant exemplary configuration, the pullout configuration may include a 5V line 72, a ground line 74, and various signal interfaces corresponding to serial peripheral interface (SPI) pins. These may include a synchronous clock (SCK) 76 pin, a master input/slave output (MISO) 78 pin, a master output/slave input (MOSI) 80 pin, and a chip select (CS) pin 82. The SCK 76 may provide a serial clock input from the patient monitor 12 to the sensor-monitor intercommunication cable 20. The MISO 78 may transmit synchronous serial data, such as physiological measurements determined in the monitor-side cable connector 28, from the sensor-monitor intercommunication cable 20 to the patient monitor 12. The MOSI 80 may transmit synchronous serial data, such as sensor control signals, from the patient monitor 12 to the sensor-monitor intercommunication cable 20. The patient monitor 12 may use the CS 82 to elect to communicate with the sensor-monitor intercommunication cable 20. To reduce pin count, the CS signal 82 may be omitted from the connector and tied to ground (active low) at the slave side if there is only one master and one slave on the bus. The cable may be designed such that either the monitor 12 or the sensor-monitor intercommunication cable 20 is the SPI bus master. In this way, the configuration illustrated in FIG. 5 may enable the patient monitor 12 to control a number of different sensors 14 coupled via similar SPI configurations and sensor-monitor intercommunication cables 20.

Figure 6:
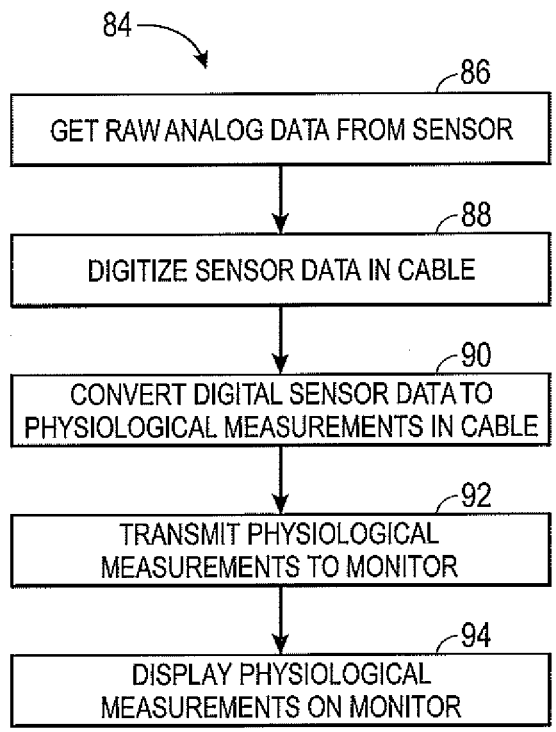
FIG. 6 is a flowchart describing an embodiment of a method for processing sensor data in a patient cable.

FIG. 6 is a flowchart 84 describing an embodiment of a method for communicably coupling the medical sensor 14 to the patient monitor 12 via the sensor-monitor intercommunication cable 20. In particular, the embodiment of the method of the flowchart 84 contemplates a sensor-monitor intercommunication cable 20 that includes the microprocessor 56, as well as appropriate software instructions stored within the ROM 60 or the nonvolatile memory 62. Because the sensor-monitor intercommunication cable 20 includes the processor 56, the patient monitor 12 need not include a processor capable of extracting physiological measurements based on data from the sensor 14. Rather, the patient monitor 12 may require only the capability to display data received from the sensor-monitor intercommunication cable 20. The flowchart 84 may be carried out using the embodiment of FIG. 3, as well as embodiments with similar capabilities, such as those described below with reference to FIGS. 9 and 10.

In a first step 86, the sensor-monitor intercommunication cable 20 may obtain analog raw data from the sensor 14. Depending on the medical sensor 14, such analog data may include, for example, photoplethysmographic data, temperature data, respiration data, blood pressure data, arrhythmia data, ECG data, pulse transit time data, and so forth. By way of example, the analog raw data may be received by the sensor-side cable connector 24. In step 88, the raw analog data may be digitized by the sensor-monitor intercommunication cable 20 to obtain digitized raw data. If the analog raw data is a photoplethysmographic signal, the digitized raw data may be, for example, a raw 16-bit digital stream of photoplethysmographic data sampled at 100 Hz. Such digitization may take place via the sensor interface circuitry 42 in the sensor-side cable connector 24.

In step 90, the sensor-monitor intercommunication cable 20 may convert the digitized raw data into physiological measurements. By way of example, if the digitized raw data is photoplethysmographic data, the physiological measurements may include pulse rate, blood oxygen saturation, and/or total hemoglobin measurements. The physiological measurements may be obtained by the processing the digitized raw data using the microprocessor 56, according to instructions stored in the ROM 60 or nonvolatile memory 62. These physiological measurements may be transmitted to the patient monitor 12 in step 92, and displayed on the patient monitor 12 in step 94. The sensor-monitor intercommunication cable 20 may communicate with the electronic patient monitor 12 using messages of a protocol understandable by the electronic patient monitor 12. The protocol may be indicated by a selection made by the button or switch 25, or may be determined automatically by the sensor-monitor intercommunication cable 20, as described below with reference to FIGS. 12 and 13. In this way, the sensor-monitor intercommunication cable 20 may not need to be specific to a manufacturer or vendor.

In some embodiments, the physiological measurements obtained in step 90 may be used to determine alarm status. For example, the patient monitor 12 may indicate alarm limits for certain detectable physiological parameters to the sensor-monitor intercommunication cable 20. If the physiological measurements obtained in step 90 exceed the alarm limits (e.g., if heart rate or $SpO_2$ exceed a predetermined range), the sensor-monitor intercommunication cable 20 may respond accordingly. For example, in step 92, the sensor-monitor intercommunication cable 20 may transmit such an alarm to the patient monitor 12 in step 92.

Figure 7:
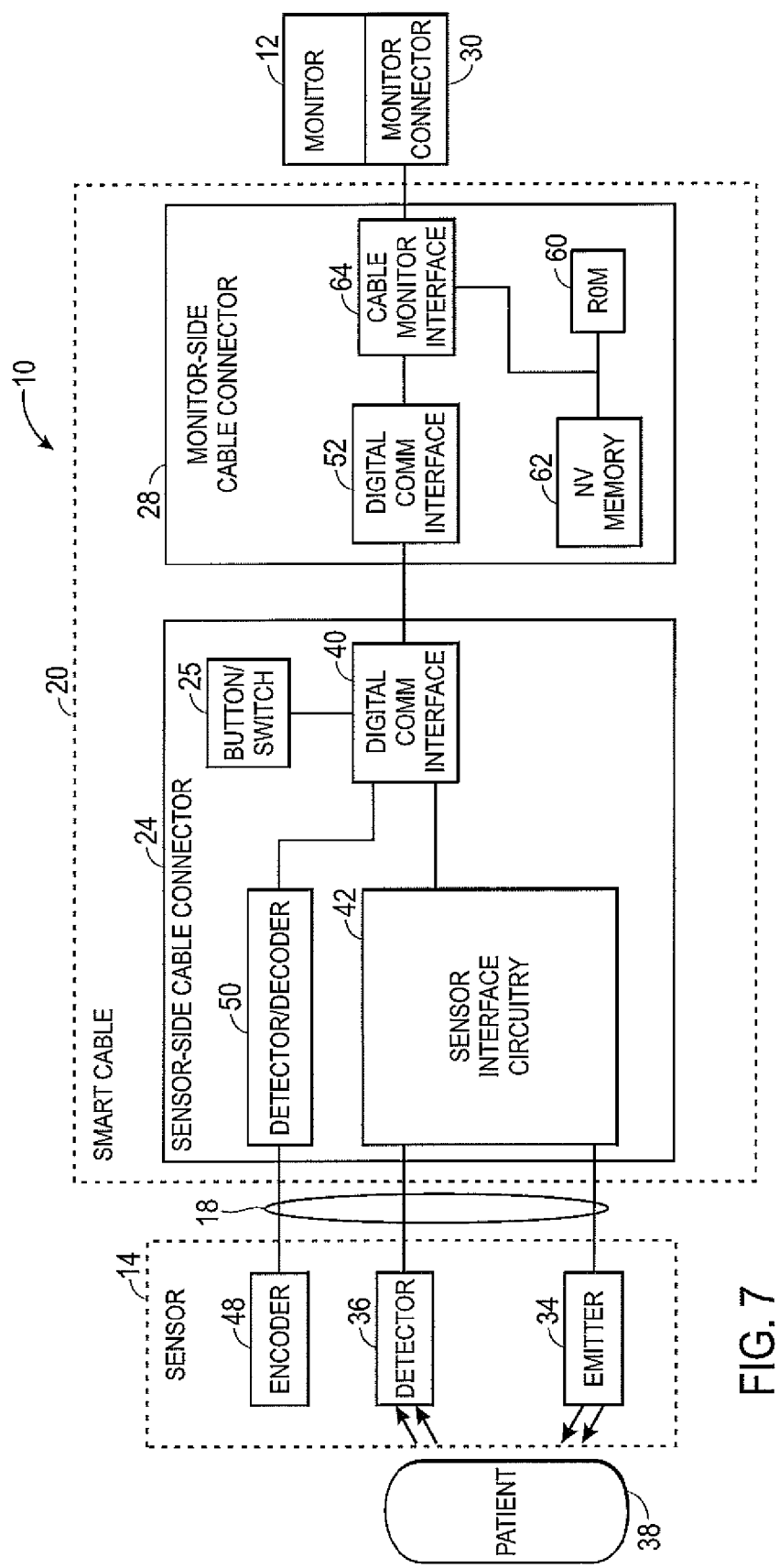
FIG. 7 is a block diagram of an alternative system of FIG. 1, in accordance with an embodiment.

As noted above, the circuitry and capabilities of the sensor-monitor intercommunication cable 20 may vary. FIG. 7 illustrates an alternative embodiment of the system 10, in which the sensor-monitor intercommunication cable 20 is capable of digitizing sensor 14 data, but lacks the ability to process the digitized data into physiological measurements on its own. In particular, the embodiment of the system 10 illustrated in FIG. 7 may be substantially identical to the embodiment of the system 10 illustrated in FIG. 3, except that the monitor-side cable connector 28 may lack the microprocessor 56 and/or RAM 58. When used with a patient monitor 12 having a suitable processor, however, the sensor-monitor intercommunication cable 20 may provide the patient monitor 12 with software instructions for obtaining such physiological measurements. Such instructions may be stored, for example, in the ROM 60 or the nonvolatile memory 62. After receiving the software instructions from the sensor-monitor intercommunication cable 20, the patient monitor 12 may thereafter obtain the physiological measurements based on digitized raw data received from the sensor-monitor intercommunication cable 20.

Figure 8:
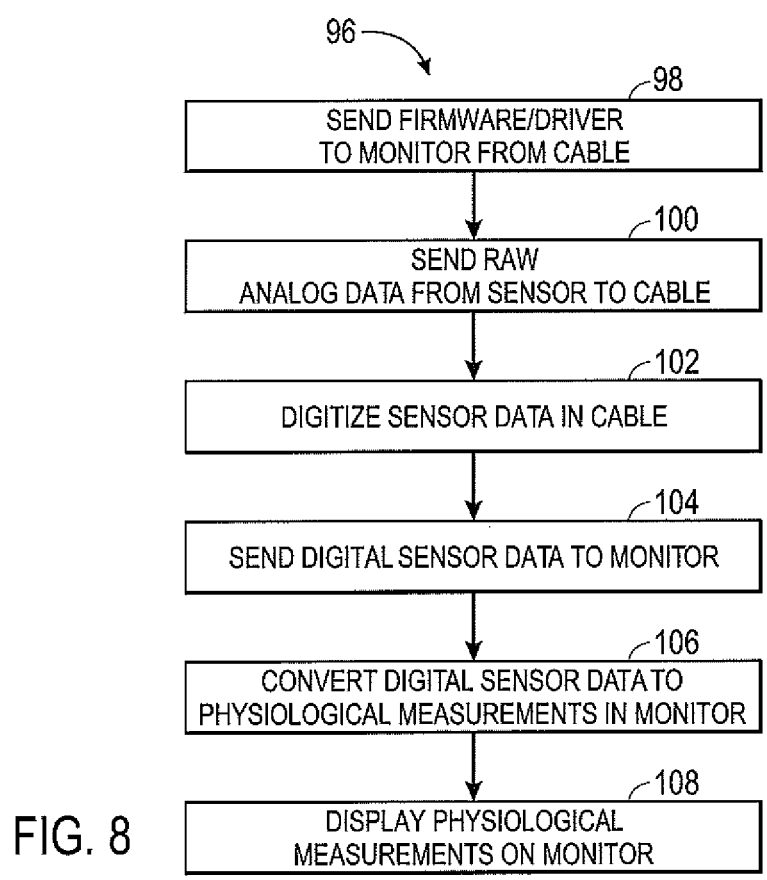
FIG. 8 is a flowchart of an embodiment of a method for processing sensor data in a patient monitor based on instructions from a patient cable.

A flowchart 96, illustrated in FIG. 8, describes an embodiment of a method for processing medical sensor 14 data in the patient monitor 12 using software instructions provided by the sensor-monitor intercommunication cable 20. The embodiment of the method of the flowchart 96 may be performed using either of the embodiments of the sensor-monitor intercommunication cable 20 described in FIG. 3 or FIG. 7, as well as the embodiments of similar circuitry with similar capabilities described below with reference to FIGS. 9 and 10. The electronic patient monitor 12 should include a processor capable of obtaining physiological measurements from digitized raw data, when provided the appropriate software.

In a first step 98, the sensor-monitor intercommunication cable 20 may send software instructions for obtaining physiological measurements from raw data, which may be in the form of firmware or a driver, to the electronic patient monitor 12. Step 98 may take place, for example, when the electronic patient monitor boots up from an SPI flash memory device, or boot memory, located in the sensor-monitor intercommunication cable 20. In step 100, the sensor-monitor intercommunication cable 20 may receive analog raw data from the sensor 14, in generally the same manner as described with reference to step 86 of the flowchart 84. In step 102, the raw analog data may be digitized by the sensor-monitor intercommunication cable 20 to obtain digitized raw data, in generally the same manner as described with reference to step 88 of the flowchart 84.

In step 104, the digitized raw data may be transmitted to the electronic patient monitor 12 in a particular protocol understandable to the monitor 12. A practitioner may select the protocol via the button or switch 25, the sensor-monitor intercommunication cable 20 may be preprogrammed to communicate using the protocol, or the sensor-monitor intercommunication cable 20 may automatically select the proper protocol, as described below with reference to FIGS. 12 and 13. Using the firmware or driver received in step 98, in step 106, the monitor 12 may process the digitized raw data to obtain physiological measurements, such as pulse rate, blood oxygen saturation, and/or a measurement of total hemoglobin. In step 108, the patient monitor 12 may display the physiological measurements on the display 16.

Figure 9:
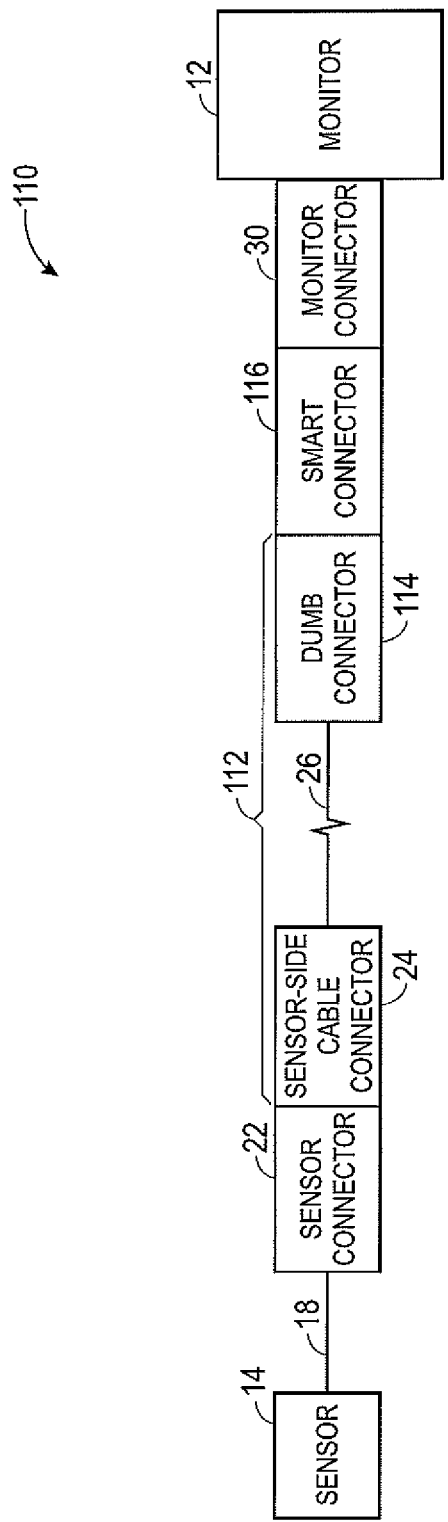
FIG. 9 is a block diagram of an alternative system for providing sensor data to a patient monitor, in accordance with an embodiment.
Figure 10:
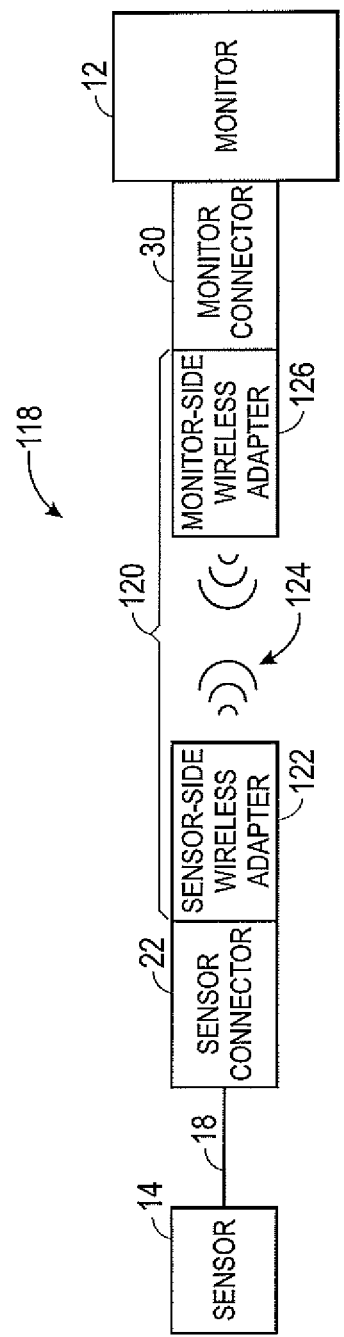
FIG. 10 is a block diagram describing the system of FIG. 9 in greater detail, in accordance with an embodiment.

FIGS. 9 and 10 represent alternative systems for intercommunication between the medical sensor 14 and the electronic patient monitor 12. In particular, FIG. 9 illustrates a system employing the techniques described herein using an additional cable connector with memory or processing circuitry, and FIG. 10 illustrates a system employing the techniques described herein using wireless communication in place of the digital cable 26. Turning first to FIG. 9, a system 110 for intercommunication between the medical sensor 14 and the patient monitor 12 may include a digitizing cable 112 coupled to the sensor connector 22 of the analog cable 18. The digitizing cable 112 may include the sensor-side cable connector 24, which may be configured in the manners described above. Rather than include a monitor-side cable connector 28 with memory or processing circuitry, the digitizing cable may include a dumb connector 114 that may only transfer digital signals in the manner received from the sensor-side cable connector 24. Thus, the digitizing cable 112 may simply digitize analog raw data received from the medical sensor 14 into digital raw data.

In contrast, a smart connector 116 may include memory circuitry and/or processing circuitry for obtaining physiological measurements from digitized raw data. As such, the smart connector 116 may include substantially the same circuitry as the monitor-side cable connector 28, as illustrated in FIG. 3 or 7. The smart connector 116 may couple to the dumb connector 114 of the digitizing cable 112 using any suitable manner to supply power to and exchange digital communication with the digitizing cable 112. In general, the smart connector 116 may interconnect with the dumb connector 114 in substantially the same way as the monitor-side cable connector 28 with the monitor connector 30 in the system 10. The smart connector 116 may interconnect with the monitor connector 30 in much the same way. As such, the smart connector 116 may employ a digital communication interface such as a serial peripheral interface (SPI), a universal serial bus (USB) interface, a universal asynchronous receiver/transmitter (UART) interface, or an RS232 interface, or any other suitable communication link. In particular, the interface between the smart connector 116 and the monitor connector 30 may be a data link.

FIG. 10 illustrates a sensor-monitor intercommunication link system 118 for intercommunication between the medical sensor 14 and the patient monitor 12 that may include wireless communication circuitry. Functioning largely like the system 10, the system 118 may include sensor-monitor wireless communication link 120 in place of the sensor-monitor intercommunication cable 20. A sensor-side wireless adapter 122 may establish wireless communication 124 with a monitor-side wireless adapter 126 using any suitable protocol. By way of example, the protocol may include the IEEE 802.15.4 standard, and may employ, for example, the ZigBee, WirelessHART, or MiWi protocols. Additionally or alternatively, the protocol may include the Bluetooth standard or one or more of the IEEE 802.11 standards. In some embodiments, the wireless communication 124 may include optical communication, such as free space optics (FSO).

The sensor-side wireless adapter 122 and the monitor-side wireless adapter 126 may include substantially the same circuitry as the sensor-side cable connector 24 and the monitor-side cable connector 28, respectively, except that the digital communication interfaces 40 and 52 may be configured for wireless communication and may include one or more rechargeable or replaceable batteries. The monitor-side wireless adapter 126 may couple to the monitor connector 30 in the same manner as the monitor-side cable connector 28 or the smart connector 116. It should be understood that the wireless interface may, additionally or alternatively, form part of the monitor 12. With such embodiments, the external connector 30 may be omitted. Also, in some embodiments, the sensor 14 may employ a single microcontroller without connector 22, whereby the microcontroller may sample the data obtained by the sensor and may also provide the processing required for wireless communication.

Like the system 10 discussed above, the systems 110 of FIG. 9 and 118 of FIG. 10 may similarly enable rapid dispersion of improvements in sensor 14 processing techniques that may otherwise require an upgraded OEM module for the patient monitor 12. Thus, rather than supply a new OEM module, a vendor may supply a sensor-monitor intercommunication cable 20, a smart connector 116, or a monitor-side wireless adapter 126 with upgraded circuitry. The new sensor-monitor intercommunication cable 20, smart connector 116, or monitor-side wireless adapter 126 may be capable of processing digitized data to obtain physiological measurements or of providing such instructions to the patient monitor 12, as described above.

Figure 11:
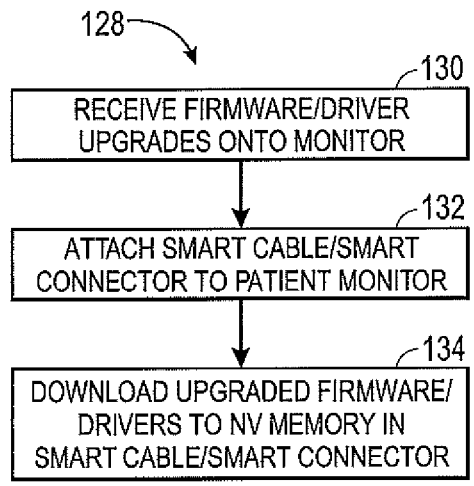
FIG. 11 is a flowchart describing an embodiment of a method for upgrading firmware in a patient cable.

In certain embodiments of the systems 10, 110, or 118, the sensor-monitor intercommunication cable 20, smart connector 116, or monitor-side wireless adapter 126 may be upgradeable via software updates from a networked electronic patient monitor. FIG. 11 is a flowchart 128 illustrating one embodiment of a method for upgrading a sensor-monitor intercommunication cable 20, smart connector 116, or monitor-side wireless adapter 126. In a first step 130, software updates, such as firmware or driver updates, may be downloaded onto a networked electronic patient monitor 12. In step 132, the sensor-monitor intercommunication cable 20, smart connector 116, or monitor-side wireless adapter 126 may be attached to the electronic patient monitor 12. In step 134, the electronic patient monitor may upload the firmware or driver to the nonvolatile memory 62 of the sensor-monitor intercommunication cable 20, smart connector 116, or monitor-side wireless adapter 126. It should be understood that the software upgrades provided in the flowchart 128 may enable various additional or alternative methods for determining the physiological parameters from the digital raw data. Additionally or alternatively, the software upgrades may enable the sensor-monitor intercommunication cable 20, smart connector 116, or monitor-side wireless adapter 126 to send and/or receive messages in a particular medical messaging protocol. It should further be understood that the flowchart 128 may alternatively be carried out by connecting the sensor-monitor intercommunication cable 20, smart connector 116, or monitor-side wireless adapter 126 to a special- or general-purpose computer rather than the electronic patient monitor 12.

As noted above, the sensor-monitor intercommunication cable 20, smart connector 116, or monitor-side wireless adapter 126 may communicate with the electronic patient monitor 12 using a specific protocol, such as the Standard Host Interface Protocol (SHIP) or the Phillips Interface Protocol (PIP). The specific protocol may be selectable by a practitioner via, for example, the button or switch 25 or by programming the cable with particular firmware or drivers. Additionally or alternatively, the monitor 12, the sensor-monitor intercommunication cable 20, smart connector 116, or monitor-side wireless adapter 126 may automatically select the proper protocol for communication with the electronic patient monitor 12. FIGS. 12-17 are flowcharts representing embodiments of methods for automatically selecting such a protocol for use in the sensor-monitor intercommunication cable 20, smart connector 116, or monitor-side wireless adapter 126.

Figure 12:
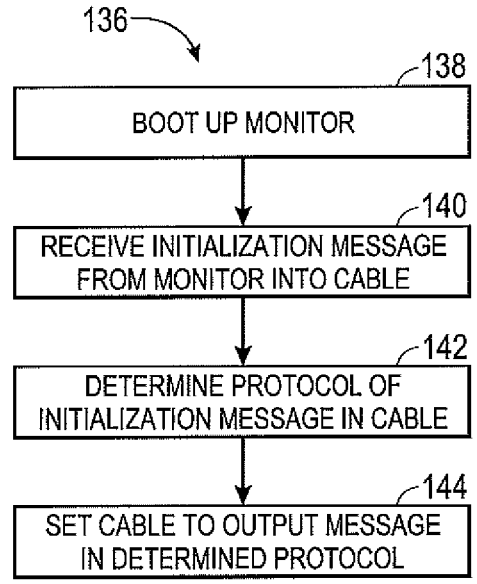

Specifically, FIG. 12 is a flowchart 136 representing an embodiment of a method for automatically selecting a protocol in the sensor-monitor intercommunication cable 20, smart connector 116, or monitor-side wireless adapter 126 based on an initialization message from the electronic patient monitor 12. In a first step 138, the monitor 12 may be initialized, During an initialization procedure, the monitor 12 may send one or more initialization messages to each of the sensors that may be coupled to the monitor 12 in step 140. After receiving the initialization messages in step 140, in step 142, the sensor-monitor intercommunication cable 20, smart connector 116, or monitor-side wireless adapter 126 may determine the protocol in which the initialization message is encoded. The determination of step 142 may involve, for example, a comparison of initialization messages of various protocols stored in the ROM 60 or the nonvolatile memory 62, or an analysis of the syntax or semantics of the initialization message. After the protocol of the monitor 12 has been determined in step 142, the sensor-monitor intercommunication cable 20, smart connector 116, or monitor-side wireless adapter 126 may store the determined protocol in the RAM 58 or the nonvolatile storage 62. Thereafter, the sensor-monitor intercommunication cable 20, smart connector 116, or monitor-side wireless adapter 126 may communicate with the electronic patient monitor 12 using a protocol that the electronic patient monitor understands.

Figure 13:
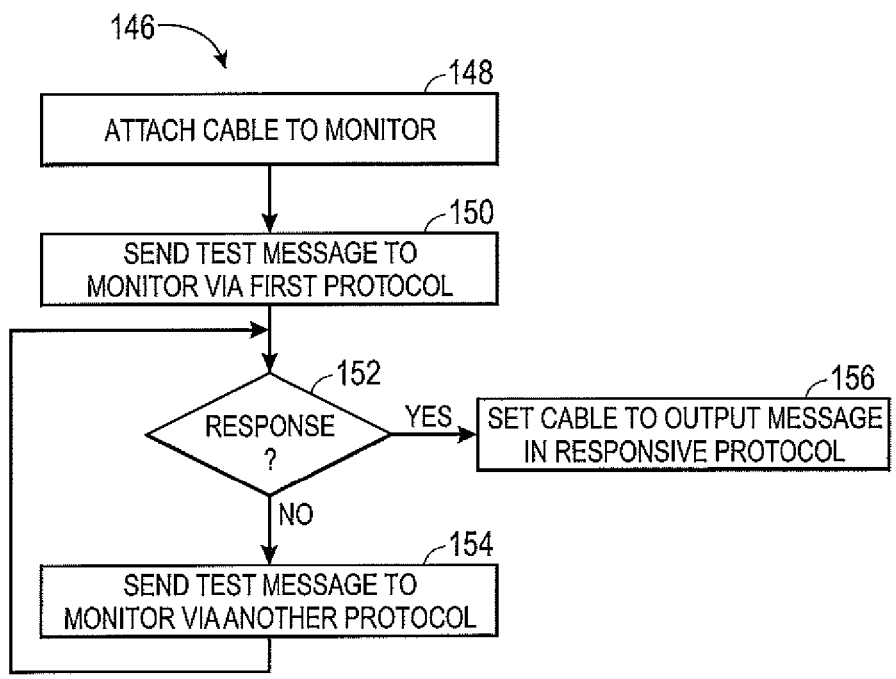

Similarly, FIG. 13 is a flowchart 146 representing an embodiment of a method for automatically selecting a protocol in the sensor-monitor intercommunication cable 20, smart connector 116, or monitor-side wireless adapter 126 based on the response to messages sent using a variety of protocols. In a first step 148, the sensor-monitor intercommunication cable 20, smart connector 116, or monitor-side wireless adapter 126 may be connected to the electronic patient monitor 12. The sensor-monitor intercommunication cable 20, smart connector 116, or monitor-side wireless adapter 126 may transmit a test message in a first protocol in step 150. By way of example, the first protocol may be the Standard Host Interface Protocol (SHIP).

As illustrated by a decision block 152, if the electronic patient monitor 12 does not understand the first protocol, the electronic patient monitor 12 may not respond or may respond with an error message. If so, after a timing-out period, in step 154, the sensor-monitor intercommunication cable 20, smart connector 116, or monitor-side wireless adapter 126 may send a second test message in a second protocol. By way of example, the second protocol may be the Phillips Interface Protocol (PIP).

Returning to the decision block 152, if the electronic patient monitor 12 does understand the second protocol, the electronic patient monitor 12 may respond with a message other than an error message. If so, in step 156, the sensor-monitor intercommunication cable 20, smart connector 116, or monitor-side wireless adapter 126 may store the protocol that achieved a non-error message response from the monitor 12 in the RAM 58 or nonvolatile storage 62. On the other hand, if the electronic patient monitor 12 does not understand the second protocol, the sensor-monitor intercommunication cable 20, smart connector 116, or monitor-side wireless adapter 126 may continue to send test messages in various protocols, which may be preprogrammed in the ROM 60 or nonvolatile storage 62, until the electronic patient monitor 12 responds favorably.

The sensor-monitor intercommunication cable 20, smart connector 116, or monitor-side wireless adapter 126 may discern whether a response from the electronic patient monitor 12 is valid in any suitable manner. For example, the sensor-monitor intercommunication cable 20, smart connector 116, or monitor-side wireless adapter 126 may send test messages in every protocol preprogrammed in ROM 60 or nonvolatile storage 62 and store the responses from the monitor 12. If certain responses differ from other responses, and particularly if one response is different from all other responses, the sensor-monitor intercommunication cable 20, smart connector 116, or monitor-side wireless adapter 126 may determine that the other responses are error messages and the different response(s) is a normal response. Alternatively, the sensor-monitor intercommunication cable 20, smart connector 116, or monitor-side wireless adapter 126 may compare the responses as they arrive to stored error messages in the ROM 60 or nonvolatile storage 62 to determine what responses from the electronic patient monitor 12 are normal responses indicating that the monitor 12 understands the protocol of the test message and which responses are error messages indicating that the monitor 12 does not understand the protocol of the test message. In some embodiments, the sensor-monitor intercommunication cable 20 may send an intentionally errored message to the monitor 12. The protocol of the monitor 12 can be narrowed down based on whether the monitor 12 replies to errored messages and/or the format of the response. Certain protocols (e.g. SHIP) may have one or more SYNC byte(s) to start a message and cyclic redundancy check (CRC) for error checking, which may reduce ambiguity in determining whether a message from the monitor 12 is valid.

FIG. 14 is a flowchart 158 representing an embodiment of a method for automatically selecting a protocol in the sensor-monitor intercommunication cable 20, smart connector 116, or monitor-side wireless adapter 126 based on the response to messages sent using a variety of protocols. In a first step 160, the sensor-monitor intercommunication cable 20, smart connector 116, or monitor-side wireless adapter 126 may be connected to the electronic patient monitor 12. In step 162, the sensor-monitor intercommunication cable 20, smart connector 116, or monitor-side wireless adapter 126 may recall the most recently negotiated protocol, which may have been stored in non-volatile storage 62. The sensor-monitor intercommunication cable 20, smart connector 116, or monitor-side wireless adapter 126 may transmit a test message in the recalled protocol in step 164. Thereafter, decision block 166 and steps 168 and 170 may take place in substantially the same manner as decision block 152 and steps 154 and 156 of the flowchart 146 of FIG. 13.

FIG. 15 is a flowchart 172 representing an embodiment of a method for automatically selecting a protocol in the sensor-monitor intercommunication cable 20, smart connector 116, or monitor-side wireless adapter 126 based on a configuration message from the patient monitor 12. In a first step 174, the sensor-monitor intercommunication cable 20, smart connector 116, or monitor-side wireless adapter 126 may be connected to the electronic patient monitor 12. In step 176, the patient monitor 12 may provide a configuration message. The configuration message may be provided in a format that was previously agreed upon by many or all manufacturers of patient monitors 12. The message may indicate various information regarding the operation of the patient monitor 12, including the communication protocol employed by the patient monitor 12. In step 178, the sensor-monitor intercommunication cable 20, smart connector 116, or monitor-side wireless adapter 126 may store the protocol indicated by the configuration message from the monitor 12 in the RAM 58 or nonvolatile storage 62.

FIG. 16 is a flowchart 180 representing an embodiment of a method for automatically selecting a protocol in the sensor-monitor intercommunication cable 20, smart connector 116, or monitor-side wireless adapter 126 based on a connector 18 pin identification code from the patient monitor 12. In a first step 182, the sensor-monitor intercommunication cable 20, smart connector 116, or monitor-side wireless adapter 126 may be connected to the electronic patient monitor 12. In some embodiments, certain pins of the connecter 18 of the patient monitor 12 may be connected to power or ground, or to specific resistors or voltages, which may uniquely identify the type of the patient monitor 12 or the protocol employed by the patient monitor 12. For such embodiments, in step 184, sensor-monitor intercommunication cable 20, smart connector 116, or monitor-side wireless adapter 126 may detect such a connector 18 pin identification code that may identify the communication protocol employed by the patient monitor 12. In step 186, the sensor-monitor intercommunication cable 20, smart connector 116, or monitor-side wireless adapter 126 may store the protocol indicated by the connector 18 pin identification code from the monitor 12 in the RAM 58 or nonvolatile storage 62.

Figure 17:
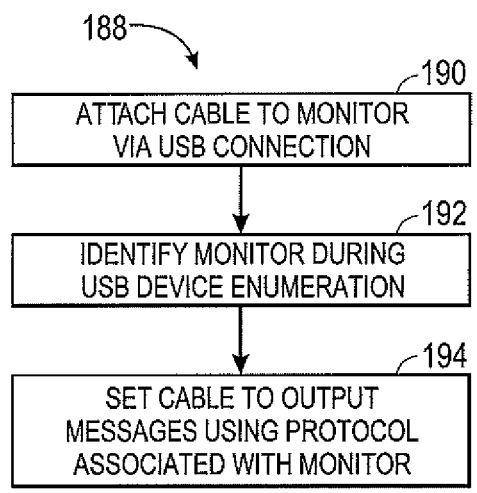

FIG. 17 is a flowchart 188 representing an embodiment of a method for automatically selecting a protocol in the sensor-monitor intercommunication cable 20, smart connector 116, or monitor-side wireless adapter 126 based on a USB device enumeration process. As noted above, in some embodiments, the sensor-monitor intercommunication cable 20, smart connector 116, or monitor-side wireless adapter 126 may be connected to the electronic patient monitor 12 via a USB connection. Such embodiments, as noted step 190, may be attached to the patient monitor 12. A USE device enumeration process may ensue. In step 192, based on information retrieved from the patient monitor 12 during the USB device enumeration process, the type of patient monitor 12 may be identified. With knowledge of the type of the patient monitor 12, the sensor-monitor intercommunication cable 20, smart connector 116, or monitor-side wireless adapter 126 may identify the protocol employed by such type of patient monitor 12. Thus, in step 186, the sensor-monitor intercommunication cable 20, smart connector 116, or monitor-side wireless adapter 126 may store the protocol indicated by the USB device enumeration process into the RAM 58 or nonvolatile storage 62.

While many of the methods for determining the communication protocol generally have been described as taking place in the sensor-monitor intercommunication cable 20, smart connector 116, or monitor-side wireless adapter 126, it should be understood that such methods may, additionally or alternatively, take place hi the patient monitor 12. That is, the patient monitor 12 may perform those actions ascribed to the sensor-monitor intercommunication cable 20, smart connector 116, or monitor-side wireless adapter 126, to determine which communication protocol to employ.

In alternative embodiments, the sensor-monitor intercommunication cable 20, smart connector 116, or monitor-side wireless adapter 126 may communicate with the electronic patient monitor 12 in other ways. For example, rather than communicate using a single protocol, the sensor-monitor intercommunication cable 20, smart connector 116, or monitor-side wireless adapter 126 may communicate a single message using several protocols, and the electronic patient monitor 12 may disregard messages not encoded in the protocol it understands. Additionally or alternatively, the sensor-monitor intercommunication cable 20, smart connector 116, or monitor-side wireless adapter 126 may output information in a universal protocol not specific to a particular vendor, or may output raw information using a protocol such as serial peripheral interface (SPI) or universal serial bus (USB).

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

What is claimed is:

1. An oximetry assembly comprising:
   a cable assembly including a proximal end and a distal end;
   an oximetry sensor located at the distal end of the cable assembly and configured to provide one or more raw oximetry signals, the oximetry sensor configured to attach to a finger and comprising at least one emitter and at least one detector, the at least one emitter configured to transmit light at one or more wavelengths into tissue, the at least one detector configured to receive the light after the light passes through or is reflected by the tissue and to output the one or more raw oximetry signals based on the received light, wherein the one or more raw oximetry signals comprise analog data;

an analog-to-digital converter housed within the cable assembly and configured to receive the one or more raw oximetry signals from the oximetry sensor and to digitize the one or more raw oximetry signals to output one or more digitized oximetry signals;

a connector located at the proximal end of the cable assembly and configured to removably couple the cable assembly to a monitor; and a processor housed within the cable assembly, wherein the processor, when in operation, receives the one or more digitized oximetry signals from the analog-to-digital converter, processes the one or more digitized oximetry signals to determine one or more oximetry measurements, and transmits the one or more oximetry measurements to the monitor when the connector is coupled to the monitor.

2. The oximetry assembly of claim 1, further comprising a non-transitory computer readable medium housed within the cable assembly, wherein the non-transitory computer readable medium includes instructions for obtaining the one or more oximetry measurements from the one or more digitized oximetry signals and for instructing the processor to perform operations on the one or more digitized oximetry signals to determine the one or more oximetry measurements, and wherein the processor, when in operation, accesses the non-transitory computer readable medium to read the instructions and executes the instructions to determine the one or more oximetry measurements.

3. The oximetry assembly of claim 1, wherein the processor, when in operation, controls the oximetry sensor.

4. The oximetry assembly of claim 1, wherein the processor, when in operation, determines the one or more oximetry measurements using one or more algorithms.

5. The oximetry assembly of claim 1, wherein the one or more oximetry measurements comprises one or more of pulse rate, blood oxygen saturation, or total hemoglobin.

6. The oximetry assembly of claim 1, wherein the processor is programmed to download software updates from a remote source.

7. An oximetry assembly comprising:

a cable assembly including a proximal end and a distal end, wherein the cable assembly comprises an analog-to-digital converter housed within the cable assembly, and wherein the analog-to-digital converter is configured to digitize the one or more raw oximetry signals;

an oximetry sensor located at the distal end of the cable assembly and configured to provide one or more raw oximetry signals, the oximetry sensor configured to attach to a finger and comprising at least one emitter and at least one detector, wherein the at least one emitter is configured to transmit light at one or more wavelengths into tissue, and the at least one detector is configured to receive the light after the light passes through or is reflected by the tissue and to output the one or more raw oximetry signals based on the received light;

a connector located at the proximal end of the cable assembly, wherein the connector is configured to removably connect the oximetry sensor to a monitor and allow communication with said monitor through a data communication link;

a non-transitory computer readable medium housed within the cable assembly and including one or more instructions for determining one or more oximetry measurements from the one or more raw oximetry signals;

and a processor housed within the cable assembly and programmed to receive the one or more raw oximetry signals from the oximetry sensor to access the non-transitory computer readable medium to read the one or more instructions, to process the one or more raw oximetry signals using the one or more instructions to determine the one or more oximetry measurements, and configured to transmit the one or more oximetry measurements to the monitor for display.

8. The oximetry assembly of claim 7, wherein the processor is programmed to control the oximetry sensor.

9. The oximetry assembly of claim 7, wherein the processor is programmed to determine the one or more oximetry measurements using one or more algorithms stored in the non-transitory computer readable medium.

10. The oximetry assembly of claim 7, wherein the one or more oximetry measurements comprises one or more of pulse rate, blood oxygen saturation, or total hemoglobin.

11. The oximetry assembly of claim 7, wherein the cable assembly includes a sensor-monitor intercommunication cable having a sensor-side cable connector and a monitor-side cable connector.

12. The oximetry assembly of claim 7, wherein the processor is programmed to download software updates from a remote source.

13. The oximetry assembly of claim 7, wherein the data communication link includes one of a serial peripheral interface (SPI), a universal serial bus (USB) interface, a universal asynchronous receiver/transmitter (UART), a two wire interface (TWI), or an RS232 interface.

* * * * *